(12) United States Patent (10) Patent No.: US 12,594,007 B2
Arndt et al. (45) Date of Patent: Apr. 7, 2026

(54) ENERGY TRANSMITTING DEVICE AND SYSTEM TO MONITOR AND TREAT TINNITUS

(71) Applicant: Circius Pharma AB, Askim (SE)

(72) Inventors: Peter Arndt, Höllviken (SE); Fredrik Westman, Staffanstrop (SE); Arash Golshenas, Malmö (SE); Ali Jehanfard, Bara (SE)

(73) Assignee: Circius Pharma AB, Askim (SE)

( * ) Notice: Subject to any disclaimer, the term of this patent is extended or adjusted under 35 U.S.C. 154(b) by 526 days.

(21) Appl. No.: 18/004,834

(22) PCT Filed: Jul. 26, 2021

(86) PCT No.: PCT/IB2021/056763
§ 371 (c)(1),
(2) Date: Jan. 9, 2023

(87) PCT Pub. No.: WO2022/023951
PCT Pub. Date: Feb. 3, 2022

(65) Prior Publication Data
US 2023/0255514 A1 Aug. 17, 2023

(30) Foreign Application Priority Data
Jul. 27, 2020 (SE) .................................... 2030236-0

(51) Int. Cl.
*A61B 5/12* (2006.01)
*A61F 11/04* (2006.01)
*A61N 2/00* (2006.01)

(52) U.S. Cl.
CPC ............. *A61B 5/128* (2013.01); *A61F 11/045* (2013.01); *A61N 2/006* (2013.01)

(58) Field of Classification Search
CPC ........... A61B 5/05; A61B 5/024; A61B 5/128; A61B 5/1455; A61B 5/6815; A61F 11/045; A61H 23/02; A61M 21/00; A61M 21/0022; A61M 21/0027; A61M 21/0072; A61N 1/0492; A61N 1/36036; A61N 2/006; A61N 5/0613; A61N 5/067; A61P 27/16
See application file for complete search history.

(56) References Cited

U.S. PATENT DOCUMENTS

| | | | |
|---|---|---|---|
| 6,358,272 | B1 | 3/2002 | Wilden |
| 10,398,897 | B2 | 9/2019 | Owen et al. |
| 10,512,750 | B1 | 12/2019 | Lewin Jessen et al. |
| 2008/0249594 | A1 | 10/2008 | Dietrich et al. |

(Continued)

FOREIGN PATENT DOCUMENTS

| | | |
|---|---|---|
| CN | 106954155 B | 7/2017 |
| WO | 2012168543 A1 | 12/2012 |

(Continued)

*Primary Examiner* — Mihir K Rayan
(74) *Attorney, Agent, or Firm* — Capitol City TechLaw

(57) ABSTRACT

Disclosed is an energy transmitting device for use in a system to monitor and treat tinnitus, comprising: a first unit that produces energy for treating said tinnitus; and a second unit that is arranged to secure and fasten said first unit against a skin of said patient, wherein, when in operation, said first unit produces said energy based on a suggested treatment for transmission to said patient through bone conductivity for treating said tinnitus.

21 Claims, 8 Drawing Sheets

(56) References Cited

U.S. PATENT DOCUMENTS

| | | | | |
|---|---|---|---|---|
| 2018/0271710 A1* | 9/2018 | Boesen | ................ | A61B 5/7203 |
| 2018/0310107 A1* | 10/2018 | Westerkull | ............. | H04R 25/60 |
| 2019/0014425 A1* | 1/2019 | Liao | .................... | H04R 5/0335 |
| 2019/0090044 A1* | 3/2019 | Boesen | ................ | G10K 11/175 |
| 2019/0163952 A1* | 5/2019 | Mueller-Wehlau | .... | A61B 5/128 |
| 2020/0001085 A1 | 1/2020 | Owen et al. | | |

FOREIGN PATENT DOCUMENTS

| | | | |
|---|---|---|---|
| WO | 2019038746 A1 | 2/2019 |
| WO | 2019157443 A1 | 8/2019 |

* cited by examiner

800

816

802

814

806

810

812

804

808

MONITOR HEALTH CONDITION OF PATIENT
1502

COLLECT PATIENT DATA ASSOCIATED WITH HEALTH
CONDITION OF PATIENT
1504

ANALYZE PATIENT DATA
1506

SUGGEST TREATMENT FOR TINNITUS
1508

GENERATE ENERGY TO TRANSMIT TO PATIENT THROUGH BONE
CONDUCTIVITY FOR TREATING TINNITUS
1510

ENERGY TRANSMITTING DEVICE AND SYSTEM TO MONITOR AND TREAT TINNITUS

This application claims priority under 35 USC 119(a)-(d) to SE patent application No. 2030236-0, which was filed on Jul. 27, 2020, the entire contents of which are incorporated herein by reference.

TECHNICAL FIELD

The present disclosure relates to energy transmitting devices for use in systems to monitor and treat tinnitus. The present disclosure also relates to systems to monitor and treat tinnitus.

BACKGROUND

Auditory dysfunction is a condition that occurs due to age-related hearing loss, ear injury, a circulatory system disorder, exposure to louder noise, exposure to chemicals/ medications, earwax blockage, or ear bone changes. The common auditory dysfunction includes tinnitus, hearing loss, hyperacusis, auditory hallucinations, misophonia, phonophobia, and/or central auditory processing disorders. Tinnitus is a type of auditory dysfunction that is characterized by the perception of sounds like ringing, clicking, hissing, humming, chirping, buzzing, whistling, whooshing, roaring, and/or whirling in the ears or head though there are no external sound sources.

The auditory dysfunction may be constant or irregular. For example, people who experience the auditory dysfunction on an irregular basis may able to continue their day-to-day activities. People who experience the auditory dysfunction daily may struggle to do their daily activities, which significantly affects their quality of daily life. The auditory dysfunction may also associate with other conditions such as stress, sleep problem, trouble concentrating, depression, and anxiety.

Existing systems or devices are available to soften the impact of the auditory dysfunction. However, once the auditory dysfunction, like tinnitus or hearing loss, has developed, there is no cure for it. Some existing approaches treat the health condition, for example, ear injury, which causes the auditory dysfunction. Some existing approaches aim to correct the inability associated with the auditory dysfunction with the help of hearing aids and masking devices.

Existing approaches use retraining therapy for effective treatment of the auditory dysfunction such as tinnitus, and hyperacusis. The retraining therapy includes stimulation of the ear with sound for a continuous period. Over a period, the retraining therapy may habituate the person to auditory dysfunction. Therefore, the person may not focus on the sounds due to the auditory dysfunction. For practical reasons, the retraining therapy is done in the night when the person receives the sound from a smartphone or other sound stimulator or hearing aid. Existing approaches that use retraining therapy may not suitable to use during daytime and may affect daily activities and hearing of the person while in use.

One existing approach that uses the retraining therapy designs a patch for reducing the discomfort of tinnitus. The patch contains a unique raster or lens that creates an organized signal which is anticipated to modulate nerve functions in the auditory system through light wave treatment. However, the patch is not reusable after usage and may cost high.

Common drawbacks to the aforementioned devices/approaches are that they are not patient specific, user friendly, ergonomic, reusable, and cost-effective. Further, the aforementioned devices/approaches may not provide treatment to the auditory dysfunctions such as tinnitus based on statistical information about the auditory dysfunctions.

Therefore, in light of the foregoing discussion, there exists a need to address the aforementioned drawbacks in existing technologies in treating auditory dysfunctions such as tinnitus without affecting the person's daily activities.

SUMMARY

The present disclosure seeks to provide an energy transmitting device for use in a system to monitor and treat tinnitus. The present disclosure also seeks to provide a system to monitor and treat tinnitus. An aim of the present disclosure is to provide a solution that overcomes at least partially the problems encountered in prior art.

In one aspect, an embodiment of the present disclosure provides an energy transmitting device for use in a system to monitor and treat tinnitus, comprising:

a first unit that produces energy for treating said tinnitus; and a second unit that is arranged to secure and fasten said first unit against a skin of said patient, wherein, when in operation, said first unit produces said energy based on a suggested treatment for transmission to said patient through bone conductivity for treating said tinnitus.

Beneficially, the energy transmitting device could treat an auditory dysfunction like tinnitus, hearing impairment, hyperacusis, auditory hallucinations, misophonia, phonophobia, and central auditory processing disorders by transmitting energy to the patient through bone conductance. The energy transmitting device treats the tinnitus without affecting the patient's daily activities.

Optionally, the second unit comprises:

an adhesive material that is arranged to attach said first unit against a skin of said patient; and an adapter having a first side and a second side, wherein said first side of said adapter is arranged to be fastened to said skin of said patient using an adhesive material, wherein, when in use, said first unit is arranged to be in contact with said skin of said patient.

Optionally, said adapter is integrated into said adhesive material for securing said first unit with said adhesive material, and is a magnetic adapter that secures said first unit through magnetism.

Alternatively, said adapter comprises a snap lock that locks said first unit within said adapter and enables removal of said first unit from said adapter after use.

Furthermore, the second unit comprises:

an adhesive material that comprises a first hole; and an adapter, which comprises a second hole, and is integrated into said adhesive material, for securing said first unit with said adhesive material, wherein said snap lock is configured to receive said first unit and lock said first unit within said adapter, and wherein the first and second holes enable said first unit, in use, to be in contact with a skin of said patient.

Optionally, said adapter, having a first side and a second side, wherein said first side of said adapter is arranged to be fastened to said skin of said patient using an adhesive material, is integrated into said adhesive material for securing said first unit with said adhesive material and comprises a lock that receives said first unit and locks said first unit within said adapter, wherein said adhesive material comprises a first side that is arranged to be in contact with said skin of said patient, and a second side that is integrated with said adapter and is in contact with said first unit, wherein, when in operation, when said adhesive material is arranged to be in contact with said skin of said patient, said first unit produces said energy based on said suggested treatment, and said adhesive material is configured to transmit said energy from said first unit to said patient through bone conductivity for treating said tinnitus.

In an embodiment, the energy transmitting device has a first portion and a second portion that is attached to said first portion to form a cavity, said energy transmitting device comprising a vibrating means accommodated in said cavity, wherein said vibrating means is arranged in a central region of said second portion and, in use, arranged to be in contact with a skin of said patient.

Optionally, said adapter is made of a flexible material for transmission of vibrations from said vibrating means to said skin of said patient.

Optionally, the energy transmitting device comprises a flexible ring that is accommodated in said cavity, and wherein said vibrating means is connected to a peripheral region of said second portion, via said flexible ring, for enabling vibration of said vibrating means.

Optionally, the energy transmitting device comprises a first conductive plate, a second conductive plate, a battery unit, a printed circuit board device, and an energy transmitting unit that are accommodated in said cavity, wherein said battery unit is accommodated between said first conductive plate and said second conductive plate, said printed circuit board device is coupled to said battery unit, said energy transmitting unit is fastened to said vibrating means, and wherein said printed circuit board device and said second conductive plate are adapted to form a ring shape for accommodating said energy transmitting unit therein.

Optionally, in the energy transmitting device, a locking ring is interposed between the first portion and the second portion.

Optionally, the energy transmitting device comprises a charging device that, in operation, charges said energy transmitting device, wherein said first portion of said energy transmitting device is to be at least partially accommodated in an indentation on a surface of said charging device for receiving an electric charge.

In another embodiment, the energy transmitting device comprises:

a first unit that comprises at least one of a first magnet or a first magnetic plate; and a second unit that comprises a magnetic adapter that is integrated into said adhesive material for securing said first unit with said adhesive material, wherein said magnetic adapter comprises at least one of a second magnet or a second magnetic plate that enables magnetic attachment between said magnetic adapter and said first magnet or said first magnetic plate of said first unit, wherein said adhesive material comprises a first side that is arranged to be in contact with said skin of said patient, and a second side that is integrated with said magnetic adapter and is in contact with said first unit, wherein said magnetic adapter is arranged to transmit said energy based on said suggested treatment to said patient through bone conductivity for treating said tinnitus.

In either of the two aforementioned embodiments, said first unit produces said energy that is selected from a group comprising of white noise, electrical energy, electromagnetic energy, or light energy.

Optionally, said first unit comprises a white noise generator that produces said white noise, wherein said white noise ranges from 20 hertz (Hz) to 20,000 Hz.

Optionally, said first unit comprises an electrostimulator that produces said electrical energy, wherein said electrical energy ranges from 45 microamperes ($\mu$A) to 100 $\mu$A.

Optionally, said first unit comprises a neurostimulator that produces said electrical energy, or said electromagnetic energy, wherein said electrical energy ranges from 45 microamperes ($\mu$A) to 100 $\mu$A, wherein said electromagnetic energy ranges from 10 hertz (Hz) to 90 Hz.

Optionally, said first unit comprises a laser emitting device that produces said light energy, wherein said light energy has a wavelength range from 600 nanometres (nm) to 1000 nm.

Optionally, said first unit that produces said energy that is selected from a group comprising of white noise, electrical energy, electromagnetic energy, or light energy comprises:

a plurality of buttons that is pre-programmed with a plurality of suggested treatment operations to treat said tinnitus; and a second processor that is configured to execute at least one of the suggested treatment operations when at least one button is actuated by said patient.

In another aspect, an embodiment of the present disclosure provides a system to monitor and treat tinnitus, characterized in that the system comprises:

a sensor unit that comprises at least one sensor to monitor health condition associated with an auditory dysfunction of a patient;

a first processor and a database to collect patient data associated with said health condition associated with said auditory dysfunction of said patient and to suggest the suggested treatment for said tinnitus to said patient based on said collected patient data; and an energy transmitting device according to the aforementioned aspect, in any of its embodiments or options.

Beneficially, the system effectively collects the patient data associated with a patient and enables in detecting a root cause of the tinnitus and in determining a new way of treatment based on the collected patient data associated with the patient. The system advantageously provides patient-specific treatment to the tinnitus based on the health condition of the patient. The system is effective, reliable and can be implemented with ease.

Optionally, the system of this aspect of the disclosure further comprises an interface that is configured for said patient to provide, to said system, subjective information pertaining to a health condition of said patient, wherein said first processor suggests the suggested treatment for said tinnitus to said patient based on said information.

Optionally, in the system of this aspect of the disclosure, said first processor predicts a change in said tinnitus that is about to happen in future based on said patient data, indicates to said patient about the change in said tinnitus that is about to happen and to said patient to handle said tinnitus in the future.

Optionally, said system further comprises an interface that enables said patient to provide information about when the changes in said tinnitus occur and transmits said information to a cloud server for analysing said information to suggest said treatment and said guidance for said tinnitus.

Optionally, the at least one sensor comprises at least one of: an accelerometer, a temperature sensor, a pulse sensor, a blood pressure sensor, and an oxygenation sensor. The sensor unit may collect a temperature, a pulse rate, a respiration rate, a movement pattern, or a blood pressure of the patient and may transmit the temperature, the pulse rate, the respiration rate, the movement pattern or the blood pressure of the patient to a user device or a cloud server.

Preferably, the first processor implements the suggested treatment by activating the energy transmitting device.

Embodiments of the present disclosure substantially eliminate or at least partially address the aforementioned problems in the prior art, and enable in monitoring and in treating tinnitus without affecting daily activities of a patient, using energy transmitting device and system to monitor and treat the tinnitus.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers. Embodiments of the present disclosure will now be described, by way of example only, with reference to the following diagrams wherein:

FIG. 3 is an exploded view of an energy transmitting device, while

Figure 1:
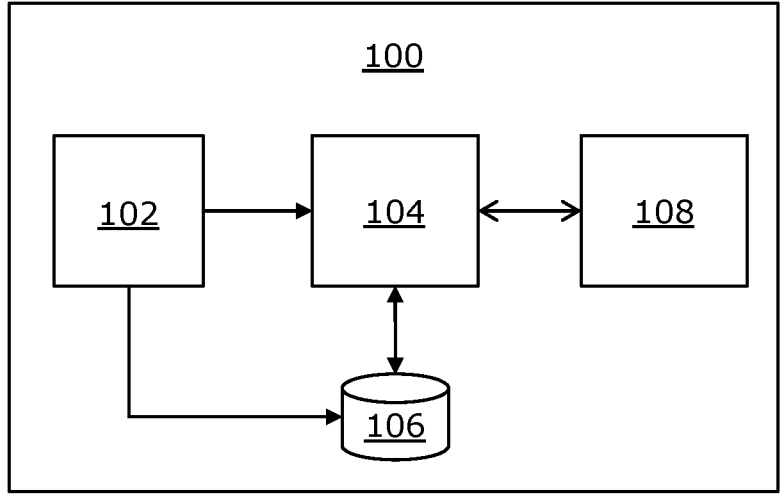
FIG. 1 is a schematic illustration of a system to monitor and treat tinnitus, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides an energy transmitting device for use in a system to monitor and treat tinnitus, comprising:

a first unit that produces energy for treating said tinnitus; and a second unit that is arranged to secure and fasten said first unit against a skin of said patient, wherein, when in operation, said first unit produces said energy based on a suggested treatment for transmission to said patient through bone conductivity for treating said tinnitus.

In another aspect, an embodiment of the present disclosure provides a system to monitor and treat tinnitus, characterized in that the system comprises:

a sensor unit that comprises at least one sensor to monitor health condition associated with an auditory dysfunction of a patient;

a first processor and a database to collect patient data associated with said health condition associated with said auditory dysfunction of said patient and to suggest the suggested treatment for said tinnitus to said patient based on said collected patient data; and an energy transmitting device according to the aforementioned aspect, in any of its embodiments or options.

The present disclosure provides the aforementioned energy transmitting device for use in a system to monitor and treat tinnitus, and the aforementioned system to monitor and treat tinnitus. The energy transmitting device could treat an auditory dysfunction like tinnitus, hearing impairment, hyperacusis, auditory hallucinations, misophonia, phonophobia, and central auditory processing disorders by transmitting energy to the patient through bone conductance. The energy transmitting device treats the tinnitus without affecting the patient's daily activities. The system effectively collects the patient data associated with a patient and enables in detecting a root cause of the tinnitus and in determining a new way of treatment based on the collected patient data associated with the patient. The system advantageously provides patient-specific treatment to the tinnitus based on the health condition of the patient. The system is effective, reliable and can be implemented with ease.

In an embodiment, the patient data associated with the health condition of the patient comprises at least one of a temperature, a pulse rate, a respiration rate, movement pattern, oxygenation rate, or a blood pressure. In an embodiment, the first unit may collect the temperature, the pulse rate, the respiration rate, the movement pattern, or the blood pressure of the patient and transmit the temperature, the pulse rate, the respiration rate, the movement pattern, or the blood pressure to a user device or the cloud server.

In an embodiment, the energy transmitting device is connected with a user device, wherein the user device adjusts the programmable settings of the energy transmitting device. In an embodiment, the user device is optionally a tablet, a desktop, a personal computer, a mobile device, an electronic notebook, or similar. In an embodiment, the energy transmitting device is connected with the user device through a network. In an embodiment, the network is a wired network. In another embodiment, the network is a wireless network. In yet another embodiment, the network is a combination of the wired network and the wireless network. In yet another embodiment, the network is the Internet.

In an embodiment, the first unit may comprise a bone conductance element for transmitting the energy to the patient through bone conductance. In an embodiment, the bone conductance element comprises a piezo-electric element or a magneto-elastic element that transmits the energy to the patient. In an embodiment, the first unit is in a shape that is selected from a group comprising of a circle, a square, a triangle or a rectangle. In an embodiment, the first unit is in contact with a skull bone of the patient.

In an embodiment, the first unit may comprise a microphone for capturing the sounds from the surroundings and a second processor that converts the sounds into an audio signal for transmitting to the patient through bone conductance. In an embodiment, the energy transmitting device may treat the hearing loss of the patient by sending the sounds from the surroundings to an inner ear of the patient through the bone conductance.

In an embodiment, the energy transmitting device may connect with one or more accessories. In an embodiment, the first unit may comprise a telecoil receiver to pick up magnetic signals and streams the magnetic signals as sound into the ears of the patient. In an embodiment, the telecoil receiver may pick up signals from a loop system that acts as an electromagnetic field and may convert the electromagnetic field into a sound signal. In an embodiment, the signal from the loop system's microphone is amplified, and background noise is removed.

In an embodiment, the second unit is a plaster or a patch. In an embodiment, the second unit is made of a material that does not affect the skin of the patient while in use. In an embodiment, the second unit may be in any shape. In an embodiment, the second unit is a disposable unit. It will be appreciated that the energy transmitting device is a wearable device. Embodiments of the energy transmitting device may be designed in a form of door opener, a key chain, a bottle opener or a toy.

Optionally, the second unit comprises:
an adhesive material that is arranged to attach said first unit against a skin of said patient; and an adapter having a first side and a second side, wherein said first side of said adapter is arranged to be fastened to said skin of said patient using an adhesive material, wherein, when in use, said first unit is arranged to be in contact with said skin of said patient.

In an embodiment, a first side of the adhesive material is in contact with the skin of the patient. In an embodiment, the first side of the adhesive material is integrated with the adapter. In an embodiment, the first unit is removable from the adapter. After removal from the adapter, the first unit may be used with a new second unit. In an embodiment, the adhesive material is a plaster or a patch. In an embodiment, the adhesive material is an energy transmitting adhesive material. In an embodiment, the adhesive material is air and moisture permeable. In an embodiment, the adhesive material is made of biodegradable material. In an embodiment, the adapter is made of biodegradable material. In an embodiment, the first unit may comprise a skin-contacting surface and a non-skin contacting surface. In an embodiment, the first unit may produce the energy when the skin-contacting surface contact with the skin of the patient. In an embodiment, the non-skin contacting surface of the first unit may face the adapter.

Optionally, said adapter having a first side and a second side, wherein said first side of said adapter is arranged to be fastened to said skin of said patient using an adhesive material, is integrated into said adhesive material for securing said first unit with said adhesive material, and is a magnetic adapter that secures said first unit through magnetism. When said adapter is integrated into said adhesive material, the adapter could be directly utilized to requisitely arrange (namely, position) the adapter to be fastened to said skin of said patient. It will be appreciated that when said adapter is the magnetic adapter, the first unit would be easily locked/removed within/from the adapter as required.

Optionally, the second unit comprises:
an adhesive material that comprises a first hole; and
an adapter, which comprises a second hole, and is integrated into said adhesive material, for securing said first unit with said adhesive material, wherein said snap lock is configured to receive said first unit and lock said first unit within said adapter, and
wherein the first and second holes enable said first unit, in use, to be in contact with a skin of said patient.

In this regard, when the adhesive material and the adapter are integrated, the first hole of the adhesive material is coincident with the second hole of the adapter. This enables said first unit to be in contact with said skin of the patient when the said first unit is secured within said adapter. Beneficially, the energy produced by said first unit could be transmitted to said patient through bone conductivity in an efficient manner and without any obstruction.

Optionally, said adapter having a first side and a second side, wherein said first side of said adapter is arranged to be fastened to said skin of said patient using an adhesive material, is integrated into said adhesive material for securing said first unit with said adhesive material and comprises a lock that receives said first unit and locks said first unit within said adapter, wherein said adhesive material comprises a first side that is arranged to be in contact with said skin of said patient, and a second side that is integrated with said adapter and is in contact with said first unit, wherein, when in operation, when said adhesive material is arranged to be in contact with said skin of said patient, said first unit produces said energy based on said suggested treatment, and said adhesive material is configured to transmit said energy from said first unit to said patient through bone conductivity for treating said tinnitus. It will be appreciated that when the lock receives and locks the first unit, the first unit is firmly positioned in a requisite manner on the skin of the patient. Owing to this, the first unit would not fall when the patient moves around in the real world, and thus the first unit could function as required (i.e., produces said energy for transmission to said patient) without hampering or affecting daily activities of the patient. In an embodiment, the lock is a snap lock or a bayonet socket lock.

Optionally, said adapter comprises a snap lock that locks said first unit within said adapter and enables removal of said first unit from said adapter after use. In an embodiment, the adapter with the snap lock may be integrated into the adhesive material. In an embodiment, the adapter with the snap lock may be integrated into a second side of the adhesive material. It will be appreciated that the adapter enables in fixing the first unit in a requisite and a constant position when in operation, and locks (or secures) the first unit within the adhesive material. The adhesive material and the adapter constitute the second unit which is disposable. In an embodiment, the energy transmitting device has a first portion and a second portion that is attached to said first portion to form a cavity, said energy transmitting device comprising a vibrating means accommodated in said cavity, wherein said vibrating means is arranged in a central region of said second portion and, in use, arranged to be in contact with a skin of said patient. In this regard, when the first unit produces said energy based on the suggested treatment, a form of said energy is converted to a vibrational energy by using the vibrating means, and then the vibrational energy is transmitted to said patient through bone conductivity for treating said tinnitus. It will be appreciated that the first portion and the second portion are fastened together using screws.

Optionally, said adapter is made of a flexible material for transmission of vibrations from said vibrating means to said skin of said patient. In this regard, the flexible material receives the vibrations from the vibrating means and since the flexible material would be in contact with the skin of the patient, the flexible material transmits said vibrations to the skin. It will be appreciated that the flexible material is non-toxic and eco-friendly material.

Optionally, the energy transmitting device comprises a flexible ring that is accommodated in said cavity, and wherein said vibrating means is connected to a peripheral region of said second portion, via said flexible ring, for enabling vibration of said vibrating means. In this regard, the vibrating means slightly protrudes from the second portion such that the vibrating means (of the first unit) is in contact with said skin of said patient. This enables the vibrating means to easily transmit the vibrational energy to said skin of said patient, when the first unit is secured within the adapter that is positioned at said skin of said patient.

Optionally, the energy transmitting device comprises a first conductive plate, a second conductive plate, a battery unit, a printed circuit board device, and an energy transmitting unit that are accommodated in said cavity, wherein said battery unit is accommodated between said first conductive plate and said second conductive plate, said printed circuit board device is coupled to said battery unit, said energy transmitting unit is fastened to said vibrating means, and wherein said printed circuit board device and said second conductive plate are adapted to form a ring shape for accommodating said energy transmitting unit therein. The first conductive plate is a first electrode of the battery unit and the second conductive plate is second electrode of the battery unit. Optionally, the battery unit serves as a power source for the energy transmitting device to function. Optionally, the battery unit comprises a lithium ion battery or a lithium polymer battery. The printed circuit board device mechanically supports and electrically connects electronic elements of the energy transmitting device using, for example, conductive tracks. It will be appreciated that the energy produced by the first unit is actually produced by the energy transmitting unit within the first unit. Optionally, when the energy transmitting unit is fastened to said vibrating means, said energy produced by the energy transmitting unit is transmitted to the vibrating means. The vibrating means converts said energy into the vibrational energy by using and then the vibrational energy is transmitted to said patient through bone conductivity for treating said tinnitus. Notably, the construction of the first unit is in a manner that the vibrating means is positioned below the energy transmitting unit. Optionally, said energy transmitting unit is fastened to said vibrating means using screws.

Optionally, the energy transmitting device comprises a charging device that, in operation, charges said energy transmitting device, wherein said first portion of said energy transmitting device is to be at least partially accommodated in an indentation on a surface of said charging device for receiving an electric charge. Optionally, in this regard, the charging device, in operation, charges the first unit. In such a case, a shape and a size of said indentation may correspond to a shape and a size of said first unit. Optionally, when charging said energy transmitting device, the battery unit of the first unit receives the electric charge. In this regard, the first portion of the first unit may be in direct contact with the surface for receiving the electric charge or may be at a predefined distance from the surface for receiving the electric charge inductively.

In another embodiment, the energy transmitting device comprises:

a first unit that comprises at least one of a first magnet or a first magnetic plate; and a second unit that comprises a magnetic adapter that is integrated into said adhesive material for securing said first unit with said adhesive material, wherein said magnetic adapter comprises at least one of a second magnet or a second magnetic plate that enables magnetic attachment between said magnetic adapter and said first magnet or said first magnetic plate of said first unit, wherein said adhesive material comprises a first side that is arranged to be in contact with said skin of said patient, and a second side that is integrated with said magnetic adapter and is in contact with said first unit, wherein said magnetic adapter is arranged to transmit said energy based on said suggested treatment to said patient through bone conductivity for treating said tinnitus.

Advantageously, the magnetic attachment between the magnetic adapter and the first unit enables energy transmission to the patient through bone conductance.

In either of the two aforementioned embodiments, said first unit optionally produces said energy that is selected from a group comprising of white noise, electrical energy, electromagnetic energy, or light energy. Beneficially, the first unit produces the aforesaid energies, based on the suggested treatment. Optionally, the first unit produces a combination of the white noise, the electrical energy, the electromagnetic energy or the light energy.

Optionally, said first unit comprises a white noise generator that produces said white noise, wherein said white noise ranges from 20 hertz (Hz) to 20,000 Hz. In an embodiment, the white noise generator may produce the white noise in a frequency range based on a condition (e.g. a hearing impairment condition) of a patient. In an embodiment, the white noise generator may be programmed according to the condition (e.g. the hearing impairment condition) of the patient to produce the white noise in one or more frequency ranges. In an embodiment, the white noise generator comprises one or more circuits to produce the white noise in a frequency range based on the condition (e.g. a hearing impairment condition) of the patient.

Optionally, said first unit comprises an electrostimulator that produces said electrical energy, wherein said electrical energy ranges from 45 microamperes (μA) to 100 μA. In an embodiment, the electrostimulator may produce the electrical energy based on a condition (e.g. a hearing impairment condition) of the patient. In an embodiment, the electrostimulator may be programmed according to the condition (e.g. the hearing impairment condition) of the patient to produce the electrical energy. In an embodiment, the electrostimulator comprises at least one voltage regulator or current regulator for regulating the electrical energy produced by a generator based on the condition (e.g. a hearing impairment condition) of the patient.

Optionally, said first unit comprises a neurostimulator that produces said electrical energy, or said electromagnetic energy, wherein said electrical energy ranges from 45 microamperes (μA) to 100 μA, wherein said electromagnetic energy ranges from 10 hertz (Hz) to 90 Hz. In an embodiment, the neurostimulator may produce the electrical energy or the electromagnetic energy based on a condition (e.g. a hearing impairment condition) of the patient. In an embodiment, the neurostimulator may be programmed according to the hearing impairment condition of the patient to produce the electrical energy or the electromagnetic energy. In an embodiment, the neurostimulator comprises at least one battery regulator or current regulator for regulating the electrical energy or the electromagnetic energy produced by a generator based on the condition (e.g. a hearing impairment condition) of the patient.

Optionally, said first unit comprises a laser emitting device that produces said light energy, wherein said light energy has a wavelength range from 600 nanometres (nm) to 1000 nm. In an embodiment, the light energy is a soft laser. In an embodiment, the laser emitting device may produce the light energy based on a condition (e.g. a hearing impairment condition) of the patient. In an embodiment, the laser emitting device may be programmed according to the condition of the patient to produce the light energy. In an embodiment, the first unit selects at least one of the white noise generator, the electrostimulator, the neurostimulator or the laser emitting device based on the suggested treatment and generates at least one of white noise, electrical energy, electromagnetic energy or light energy to treat the tinnitus.

Optionally, said first unit that produces said energy that is selected from a group comprising of white noise, electrical energy, electromagnetic energy, or light energy comprises:

a plurality of buttons that is pre-programmed with a plurality of suggested treatment operations to treat said tinnitus; and a second processor that is configured to execute at least one of the suggested treatment operations when at least one button is actuated by said patient.

In an embodiment, the plurality of buttons is a push button. In an embodiment, the plurality of operation may comprise a plurality of modes of operation. In an embodiment, the plurality of modes of operation may comprise (i) tinnitus treatment mode, (ii) hearing loss treatment mode,

12

(iii) hyperacusis treatment mode, (iv) auditory hallucination treatment mode, (v) misophonia treatment mode, (vi) phonophobia treatment mode, and/or (vii) central auditory processing disorder treatment mode. In an embodiment, at least one mode of operation is selected based on the condition of the patient. In an embodiment, the plurality of modes of operation may vary depending on the surroundings of the patient. Optionally, the plurality of buttons comprises at least one of: a power on/power off button, a reset or restart button, a volume control button.

Optionally, in the energy transmitting device, a locking ring is interposed between the first portion and the second portion. A periphery of the locking ring has a plurality of buttons of the first unit embedded thereon.

In an embodiment, the system comprises at least one input interface to receive the patient data from the sensor unit. In an embodiment, the system comprises at least one output interface to suggest the treatment for the tinnitus. It will be appreciated that the system processes the patient data received from the sensor unit to derive an energy application regimen, in a manner a requisite amount and a requisite type of energy would be produced by the energy transmitting device for transmission to said patient through bone conductivity for treating said tinnitus.

The system may also be configured to display an instruction to the patient as a suggested treatment, based upon a suggested treatment that the system has derived from input information, in particular a suggested treatment derived by the first processor and database of the system.

In an embodiment, the at least one sensor comprises at least one of: an accelerometer, a temperature sensor, a pulse sensor, a blood pressure sensor, and an oxygenation sensor. In an embodiment, the system is optionally a hearing aid, a headphone, or a data-collecting device. In an embodiment, the energy transmitting device is optionally a hearing aid, a headphone, or a data-collecting device. In an embodiment, the sensor unit may collect a temperature, a pulse rate, a respiration rate, a movement pattern, a sleep pattern, a stress pattern, or a blood pressure of the patient and may transmit the temperature, the pulse rate, the respiration rate, the movement pattern, the sleep pattern, the stress pattern, or the blood pressure of the patient to a user device or a cloud server.

In an embodiment, the sensor unit and the energy transmitting device are communicatively connected to a cloud server through a network. In an embodiment, the sensor unit transmits the patient data to the cloud server through the network. In an embodiment, the energy transmitting device may comprise a software application that transmits the patient data to the cloud server or the first processor. In an embodiment, the first processor and the database may be present in the cloud server. In an embodiment, the sensor unit comprises a transmitting unit to transmit the patient data to the cloud server. In an embodiment, the network is a wired network. In another embodiment, the network is a wireless network. In yet another embodiment, the network is a combination of the wired network and the wireless network. In yet another embodiment, the network is the Internet. In an embodiment, the cloud server is optionally a tablet, a desktop, a personal computer or an electronic notebook.

In an embodiment, the first processor and the database may be present in the cloud server. In an embodiment, the first processor and the database may be present in the energy transmitting device. In an embodiment, the database may store a plurality of patient data and treatment data associated with a plurality of auditory dysfunctions (e.g. tinnitus). In an embodiment, the cloud server analyses the patient data to suggest the treatment for the tinnitus.

Optionally, the system further comprises an interface that is configured for said patient to provide, to said system, subjective information pertaining to a health condition of said patient, wherein said first processor suggests the suggested treatment for said tinnitus to said patient based on said subjective information. It will be appreciated that the subjective information is provided by the patient via the subjective means. Optionally, the subjective information is provided in form of at least one of: a touch input, a key/button press input, a gesture input, a haptic input, a voice input, a text input. The subjective means could be a touch-sensitive device, key/button press-enabled device, a voice recording means, a text messaging means, and the like. The subjective means could be a part of the user device. The subjective information may include patient's self-experience parameters. In an example, said patient may provide information regarding how strong his/her tinnitus is. This may be done by entering a score (that lies in a range of, for example, 1 to 10) by said patient, based on his/her subjective assessment of a prevailing severity of the tinnitus he/she is experiencing.

The subjective information may alternatively not necessarily be directly associated with tinnitus. For example, an application my provide a set of general wellbeing (e.g. health condition) questions to put to the patient. Responses to these questions are fed into the first processor and database as part of the patient data.

In an embodiment, the first processor may employ at least one of the machine learning algorithm, the regression model, artificial intelligence (AI), or the neural network algorithm to determine a treatment option for the tinnitus based on the patient data. Such regression model, artificial intelligence (AI), Machine Learning or a neural network algorithm will be understood by a person skilled in the art of computer system design. It will be appreciated in embodiments of the present disclosure that the machine learning algorithm, the regression model, the AI or the neural network are trained with (i) historical patient data of a plurality of patients, (ii) auditory dysfunctions/tinnitus associated with the historical patient data of the plurality of patients, (iii) treatment provided for the auditory dysfunctions/tinnitus, and (iv) the subjective information pertaining to the health condition of said patient. It will be appreciated that the machine learning algorithm, the regression model, the AI, or the neural network algorithm would correlate/learn from the aforesaid information and would be able to predict future tinnitus attacks.

In an embodiment, the treatment comprises information of a type of energy that needs to be produced by the energy transmitting device, an amount of the energy that needs to be produced, and a duration of the energy transmission for treating the tinnitus. In an embodiment, the energy transmitting device may produce 0 to 5 Watt (W).

In an embodiment, the sensor unit is optionally a smartphone, a tablet, a desktop, a personal computer, an electronic notebook, or a smart watch. In an embodiment, the sensor unit may comprise a software application to transmit the patient data to the first processor or to the cloud server.

In an embodiment, the energy transmitting device transmits energy based on the suggested treatment for treating tinnitus in the daytime without affecting the hearing of the patient, the environment of the patient, and the self-esteem of the patient. The energy transmitting device advantageously allows the patient to perceive sounds from the surrounding when the energy transmitting device is transmitting the energy to the patient. The energy transmitting device stimulates the ear of the patient with the energy through bone conductance without blocking the ear canal of the patient.

In an embodiment, the energy transmitting device may convert the energy into a mechanical vibratory stimulus and transmits the mechanical vibratory stimulus through bone structures of the patient for treating the tinnitus. In an embodiment, the energy transmitting device may transmit the energy as a vibration signal to the patient.

Optionally, said first processor predicts a change in said tinnitus that is about to happen in future based on said patient data, indicates to said patient about the change in said tinnitus that is about to happen and to said patient to handle said tinnitus in the future.

Preferably, the first processor implements the suggested treatment by activating the energy transmitting device. In an embodiment, the first processor may employ at least one of a machine learning algorithm, a regression model, artificial intelligence (AI), or a neural network algorithm to predict changes in the tinnitus about to happen based on the collected patient data. In an embodiment, the first processor indicates to the patient that the changes in the tinnitus is going to happen and provides guidance to the patient on how to handle the situation if changes in the tinnitus happen. It will be appreciated that the first processor also provides a notification (namely, a warning) to said patient wherein the notification indicates a future attack of the tinnitus. In such a case, said patient would be aware of the future attack of the tinnitus and thereby would able to prevent said attack by receiving the suggested treatment timely.

Optionally, said system further comprises an interface that enables said patient to provide information about when the changes in said tinnitus occur and transmits said information to a cloud server for analysing said information to suggest said treatment and said guidance for said tinnitus. The interface may be provided on a linked device, such as a mobile phone, which may communicate with the first processor via a Bluetooth connection.

In an embodiment, the interface is associated with the sensor unit or the energy transmitting device. In an embodiment, the interface is a software application. In an embodiment, the cloud server receives the information about when the changes in the tinnitus occur from the patient through the interface, and analyzes the information from the patient to suggest the guidance and treatment for the tinnitus. In an embodiment, the cloud server analyses the patient data from the at least one sensor along with the information from the patient through the interface for suggesting the guidance and the treatment for the tinnitus. In an embodiment, the cloud server employs at least one of a machine learning algorithm, a regression model, artificial intelligence (AI), or a neural network algorithm to suggest the guidance and the treatment for the tinnitus.

Training for the machine learning algorithm, the regression model, the AI, or the neural network algorithm may also be provided by a direct feedback from said patient using the interface. The patient may be provided with an application to enter a score (that lies in a range of, for example, 1 to 10) based on his/her subjective assessment of the prevailing severity of tinnitus he/she is experiencing. The score is communicated into the training of the system.

In an embodiment, a method of (for) monitoring and treating tinnitus comprises:

monitoring health condition of a patient using at least one sensor;

collecting patient data associated with the health condition of the patient;

analyzing the patient data associated with the health condition of the patient based on a plurality of patient data;

suggesting treatment for the tinnitus based on the patient data;

and generating energy based on the suggested treatment to transmit the energy to the patient through bone conductivity for treating the tinnitus.

Optionally, the health condition of the patient is monitored by using the at least one sensor. The at least one sensor (of the sensing unit) senses vital parameters such as the temperature, the pulse rate, the respiration rate, the movement pattern, the sleep pattern, the stress pattern, the oxygenation rate, the blood pressure, and the like, of the patient in order to monitor the health condition of the patient. Such data is collectively presented as the patient data associated with the health condition of the patient. It will be appreciated that when the patient data is analyzed by the first processor or optionally by the cloud server, a treatment for the tinnitus is suggested.

DETAILED DESCRIPTION OF THE DRAWINGS

FIG. 1 is a schematic illustration of a system 100 to monitor and treat tinnitus, in accordance with an embodiment of the present disclosure. The system 100 comprises a sensor unit 102, a first processor 104, a database 106, and an energy transmitting device 108. In an embodiment, the system 100 may comprise a cloud server (not shown). In an embodiment, the sensor unit 102 and the energy transmitting device 108 are connected, when in operation, via a network to the cloud server. The functions of these parts has been described above. In an embodiment, the system 100 comprises an input interface (not shown) for receiving patient data from the sensor unit 102 or from the patient (not shown). In an embodiment, the system 100 comprises an output interface (not shown) for suggesting treatment for treating tinnitus. In an embodiment, the sensor unit 102 comprises a transmitting unit (not shown) to transmit the patient data to the first processor 104. In an embodiment, the sensor unit 102 comprises an application to transmit the patient data to the first processor 104. In an embodiment, the sensor unit 102 may transmit the patient data to the cloud server. In an embodiment, the first processor 104, and the database 106 may present in the cloud server.

Figure 2:
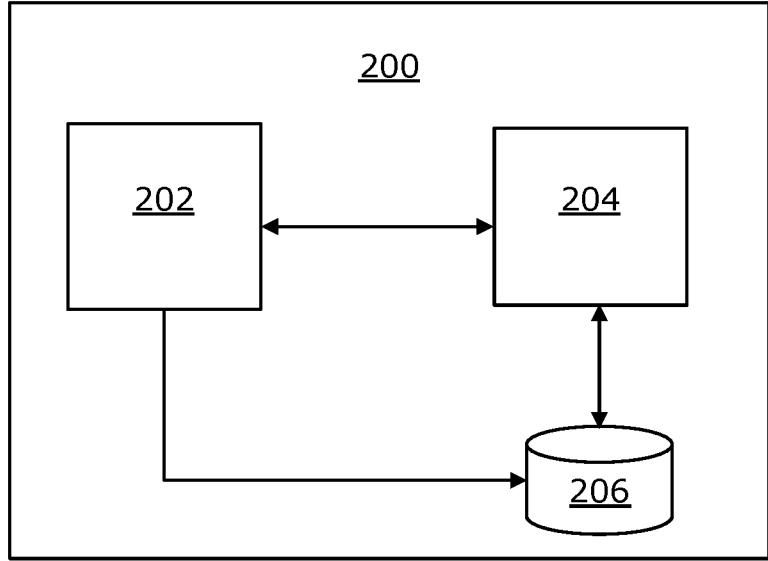
FIG. 2 is a schematic illustration of a system that includes a sensor unit as a part of an energy transmitting device, in accordance with an embodiment of the present disclosure.

FIG. 2 is a schematic illustration of a system 200 that includes a sensor unit (not shown) as a part of an energy transmitting device 202 in accordance with an embodiment of the present disclosure. The system 200 comprises an energy transmitting device 202, a first processor 204 and a database 206. In an embodiment, the energy transmitting device 202 is connected, when in operation, via a network to a cloud server.

The functions of these parts has been described above. In an embodiment, the system 200 comprises an input interface (not shown) for receiving patient data from the energy transmitting device 202 or from the patient (not shown). In an embodiment, the system 200 comprises an output interface (not shown) for suggesting treatment for treating the tinnitus. In an embodiment, the energy transmitting device 202 comprises a transmitting unit (not shown) to transmit the patient data to the first processor 204. In an embodiment, the energy transmitting device 202 comprises an application (not shown) to transmit the patient data to the cloud server.

Figure 3:
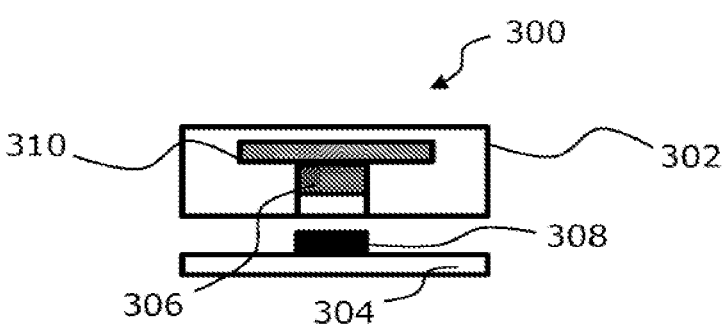
Figure 4:
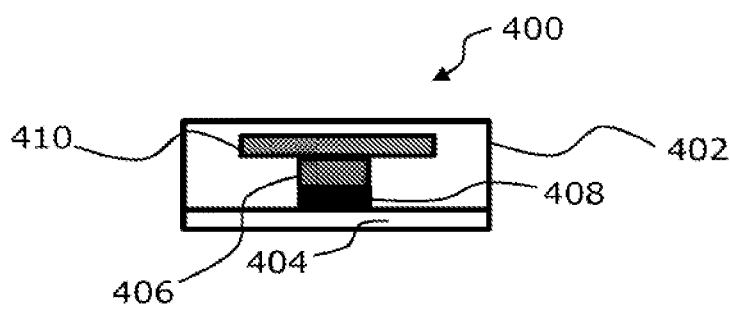
FIG. 4 is an assembled view of the energy transmitting device, in accordance with an embodiment of the present disclosure.

FIG. 3 is an exploded view of an energy transmitting device 300, while FIG. 4 is an assembled view of the energy transmitting device 400, in accordance with an embodiment of the present disclosure.

In FIG. 3, the energy transmitting device 300 comprises a first unit 302, and a second unit. The first unit 302 comprises a bone conducting element 310 and a first magnet or a first magnetic plate 306. The second unit comprises an adhesive material 304 and a magnetic adapter in a first side of the adhesive material 304. The magnetic adapter comprises a second magnet or a second magnetic plate 308 that enables magnetic attachment between the first magnet or the first magnetic plate 306 of the first unit 302 and the magnetic adapter. The first unit 302, when in operation, produces energy and the magnetic adapter transmits said energy to a patient through bone conductivity for treating tinnitus.

In FIG. 4, the energy transmitting device 400 comprises a first unit 402, and a second unit. The first unit 402 comprises a bone conducting element 410, and a first magnet or a first magnetic plate 406. The second unit comprises an adhesive material 404 and a magnetic adapter in a first side of the adhesive material 404. The magnetic adapter comprises a second magnet or a second magnetic plate 408 that enables magnetic attachment between the first magnet or the first magnetic plate 406 of the first unit 402 and the magnetic adapter. The first unit 402, when in operation, produces energy and the magnetic adapter transmits the energy to a patient through bone conductivity for treating tinnitus.

Figure 5:
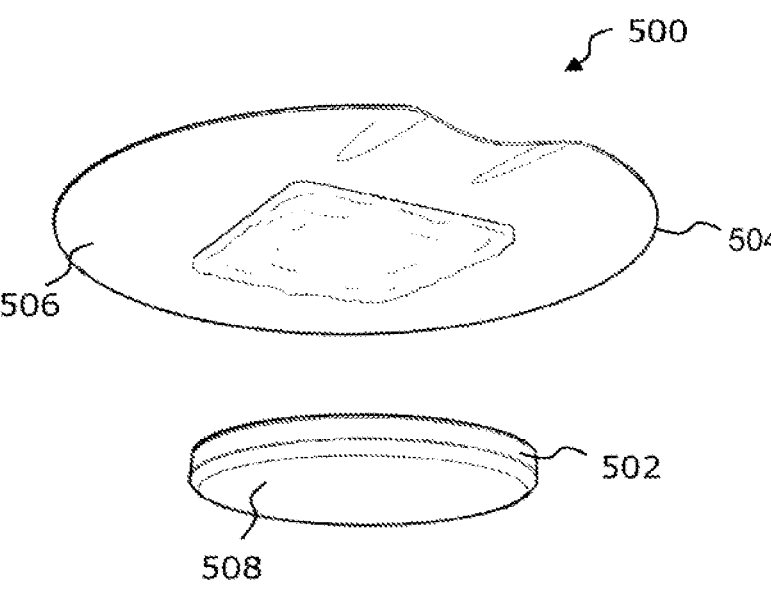
FIG. 5 is an exploded view of an energy transmitting device, in accordance with another embodiment of the present disclosure.

FIG. 5 is an exploded view of an energy transmitting device 500, in accordance with another embodiment of the present disclosure. The energy transmitting device 500 comprises a first unit 502, and a second unit 504. The first unit 502 comprises a skin-contacting surface 508, and a non-skin contacting surface (not shown). The second unit 504 comprises a first side 506 and a second side (not shown). The second unit 504 secures and fastens the first unit 502 against a skin of a person/patient. The first unit 502, when in operation, produces energy and transmits the energy to the person through bone conductivity for treating tinnitus.

Figure 6:
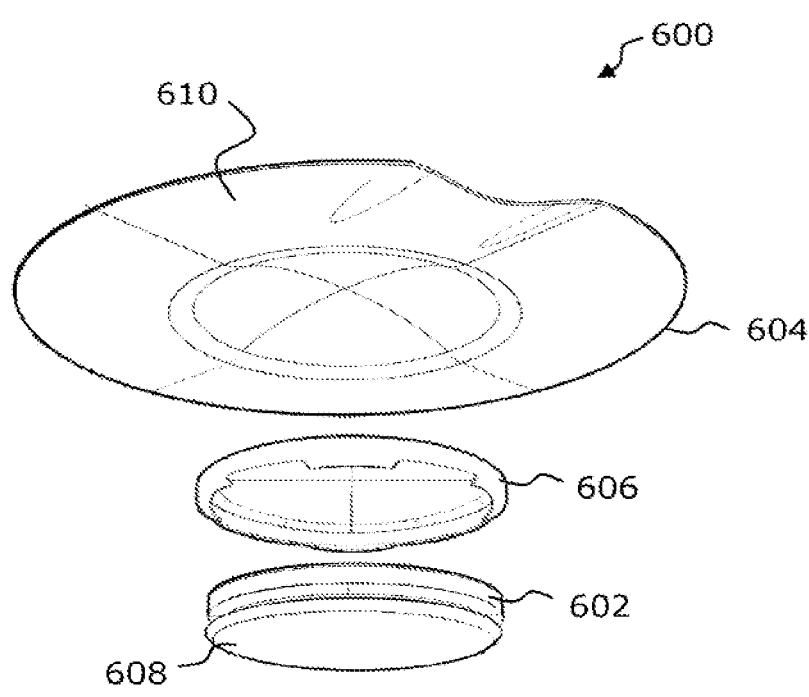
FIG. 6 is an exploded view of an energy transmitting device, in accordance with yet another embodiment of the present disclosure.

FIG. 6 is an exploded view of an energy transmitting device 600, in accordance with yet another embodiment of the present disclosure. The energy transmitting device 600 comprises a first unit 602, and a second unit comprising an adhesive material 604 and an adapter 606. The first unit 602 comprises a skin-contacting surface 608, and a non-skin contacting surface (not shown). The adhesive material 604 comprises a first side 610. The adapter 606 is integrated into the first side 610 of the adhesive material 604 for securing the first unit 602 with the adhesive material 604. The first side 610 of the adhesive material 604 attaches the first unit 602 against a skin of a person. The first unit 602, when in operation, produces energy and transmits the energy to the person through bone conductivity for treating tinnitus.

Figure 7:
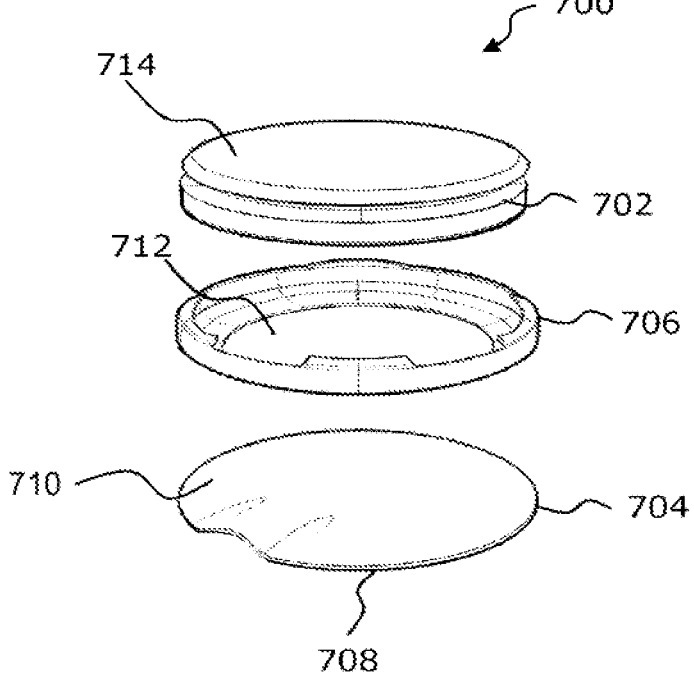
FIG. 7 is an exploded view of an energy transmitting device, in accordance with still another embodiment of the present disclosure.

FIG. 7 is an exploded view of an energy transmitting device 700, in accordance with still another embodiment of the present disclosure. The energy transmitting device 700 comprises a first unit 702, and a second unit comprising an adhesive material 704 and an adapter 706. The first unit 702 comprises an adhesive material contacting surface (not shown), and a non-adhesive material contacting surface 714. The adhesive material 704 comprises a first side 708 and a second side 710. The first side 708 of the adhesive material 704 is in contact with a skin of a patient. The adapter 706 comprises a second hole 712 for receiving the first unit 702 and is integrated into the second side 710 of the adhesive material 704 for securing the first unit 702 with the adhesive material 704. The first unit 702 is in contact with the second side 710 of the adhesive material 704 through the second hole 712 of the adapter 706. The first unit 702, when in operation, produces energy and the adhesive material 704 transmits the energy from the first unit 702 to the person through bone conductivity for treating tinnitus.

Figure 8:
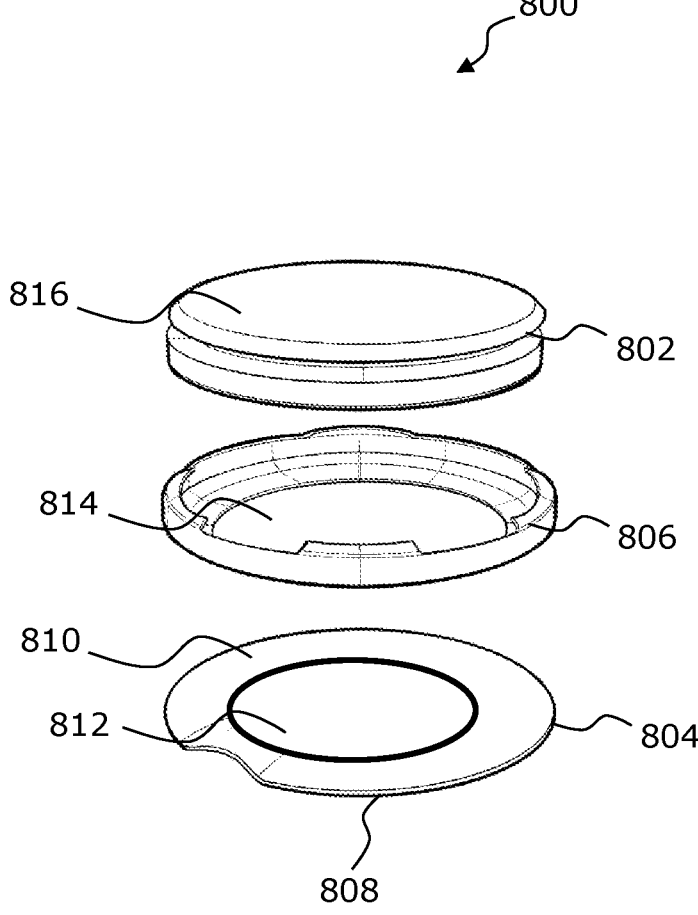
FIG. 8 is an exploded view of an energy transmitting device, in accordance with yet another embodiment of the present disclosure.

FIG. 8 is an exploded view of an energy transmitting device 800, in accordance with yet another embodiment of the present disclosure. The energy transmitting device 800 comprises a first unit 802, and a second unit comprising an adhesive material 804 and an adapter 806. The first unit 802 comprises a skin-contacting surface (not shown), and a non-skin contacting surface 816. The adhesive material 804 comprises a first side 808, a second side 810, and a first hole 812. The first side 808 of the adhesive material 804 is in contact with a skin of a person. The adapter 806 comprises a second hole 814 for receiving the first unit 802 and is integrated into the second side 810 of the adhesive material 804 for securing the first unit 802 with the adhesive material 804. The first unit 802 is in contact with a skin of the person through the first hole 812. The first unit 802, when in operation, produces energy and transmits the energy to the person through bone conductivity for treating tinnitus.

Figure 9:
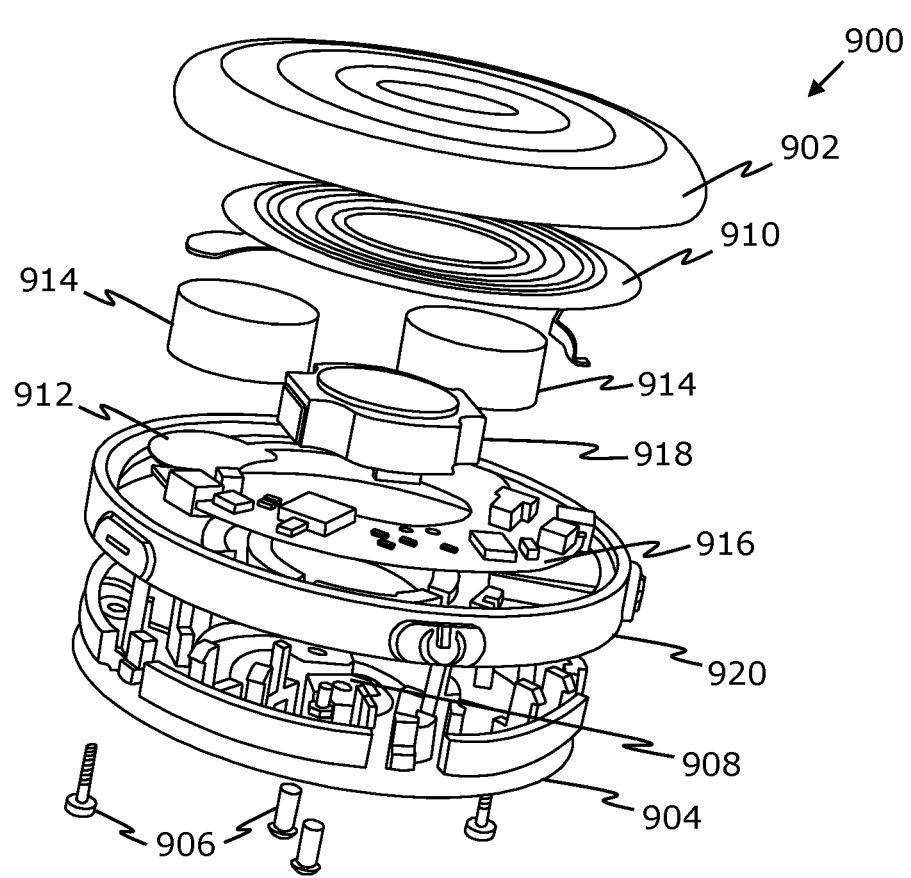
FIG. 9 is an exploded view of a first unit, in accordance with an embodiment of the present disclosure.

FIG. 9 is an exploded view of a first unit 900, in accordance with an embodiment of the present disclosure. The first unit 900 has a first portion 902 and a second portion 904 that is to be attached (by means of screws 906) to said first portion 902 to form a cavity. The first unit 900 comprises a vibrating means 908 accommodated in said cavity, wherein said vibrating means 908 is arranged in a central region of said second portion 904. The first unit 900 further comprises a flexible ring (not shown) accommodated in said cavity, and wherein said vibrating means 908 is connected to a peripheral region (not shown) of said second portion 904, via said flexible ring, for enabling vibration of said vibrating means 908. The first unit 900 further comprises a first conductive plate 910, a second conductive plate 912, a battery unit 914, a printed circuit board device 916, and an energy transmitting unit 918. All the aforesaid elements of the first unit 900 are accommodated in said cavity, wherein said battery unit 914 is accommodated between said first conductive plate 910 and said second conductive plate 912, said printed circuit board device 916 is coupled to said battery unit 914, said energy transmitting unit 918 is fastened to said vibrating means 908, and wherein said printed circuit board device 916 and said second conductive plate 912 are adapted to form a ring shape for accommodating said energy transmitting unit 918 therein. The first unit 900 further comprises a locking ring 920 that is interposed between the first portion 902 and the second portion 904.

Figure 10:
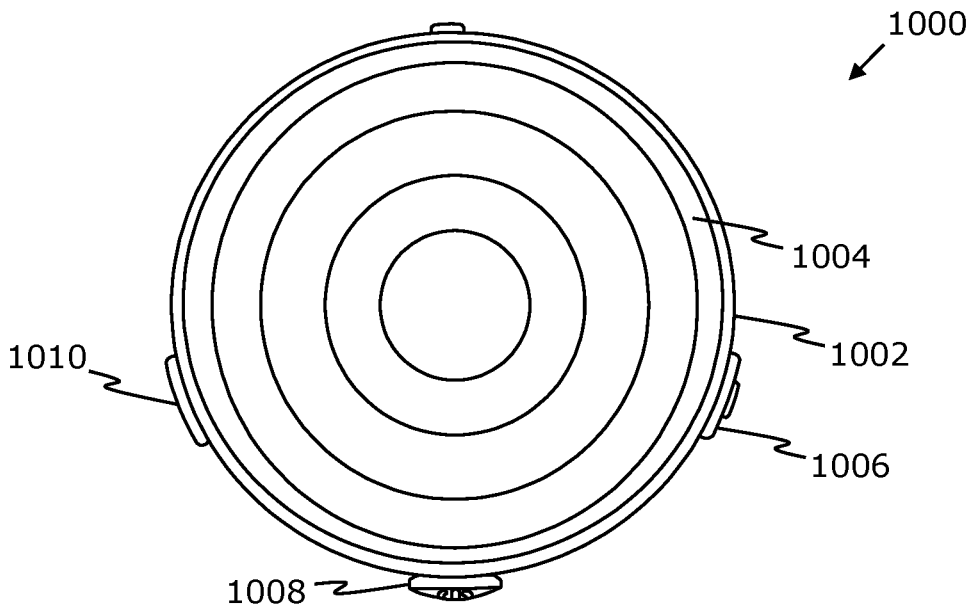
FIG. 10 is a top view of a first unit, in accordance with an embodiment of the present disclosure.

FIG. 10 is a top view of a first unit 1000, in accordance with an embodiment of the present disclosure. Herein, a shape of the first unit 1000 is circular. A locking ring 1002 is interposed between a first portion 1004 of the first unit 1000 and the second portion (not shown) of the first unit 1000. A periphery of the locking ring 1002 has buttons 1006, 1008, and 1010.

Figure 11:
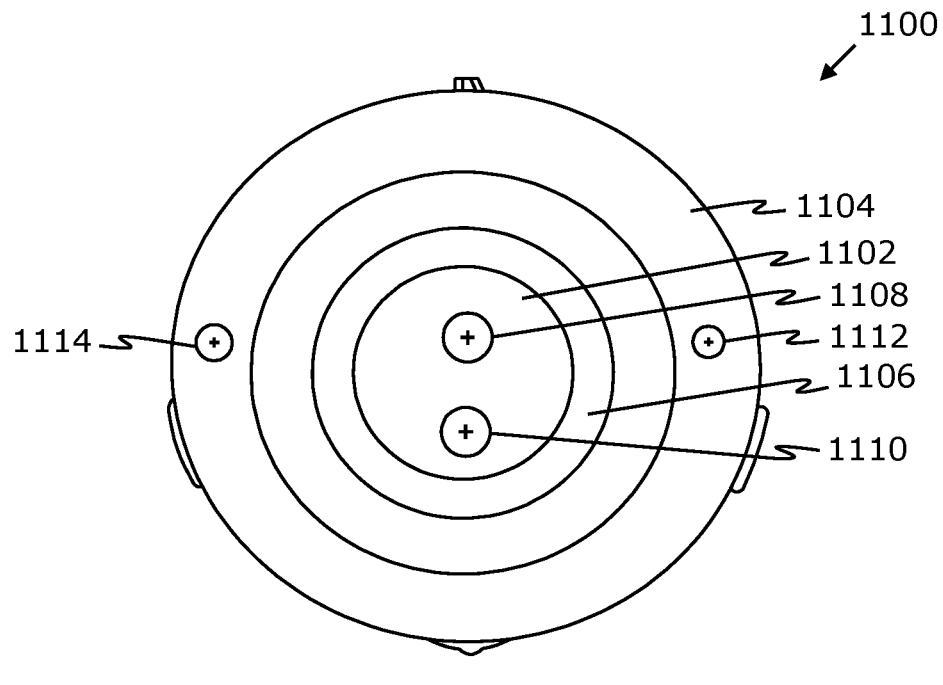
FIG. 11 is a bottom view a first unit, in accordance with an embodiment of the present disclosure.

FIG. 11 is a bottom view a first unit 1100, in accordance with an embodiment of the present disclosure. A vibrating means (not shown) within the first unit 1100 is connected to a peripheral region 1102 of a second portion 1104 of the first unit 1100, via a flexible ring 1106, for enabling vibration of said vibrating means. An energy transmitting unit (not shown) within the first unit 1100 is fastened to said vibrating means using screws 1108 and 1110. A first portion (not shown) of the first unit 1100 and the second portion 1104 are fastened using screws 1112 and 1114.

Figure 12:
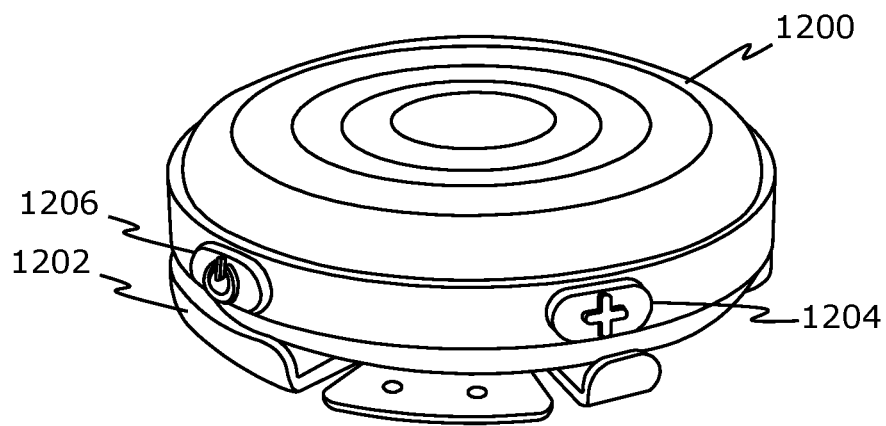
FIG. 12 illustrates a locking of a first unit and an adapter, in accordance with an embodiment of the present disclosure.

FIG. 12 illustrates a locking of a first unit 1200 and an adapter 1202, in accordance with an embodiment of the present disclosure. Herein, the first unit 1200 and the adapter 1202 are locked by means of a snap lock. The snap lock also enables removal of said first unit 1200 from said adapter 1202 as required. As shown, the first unit 1200 comprises a plurality of buttons (depicted as a volume control button 1204 and a power on/power off button 1206).

Figure 13:
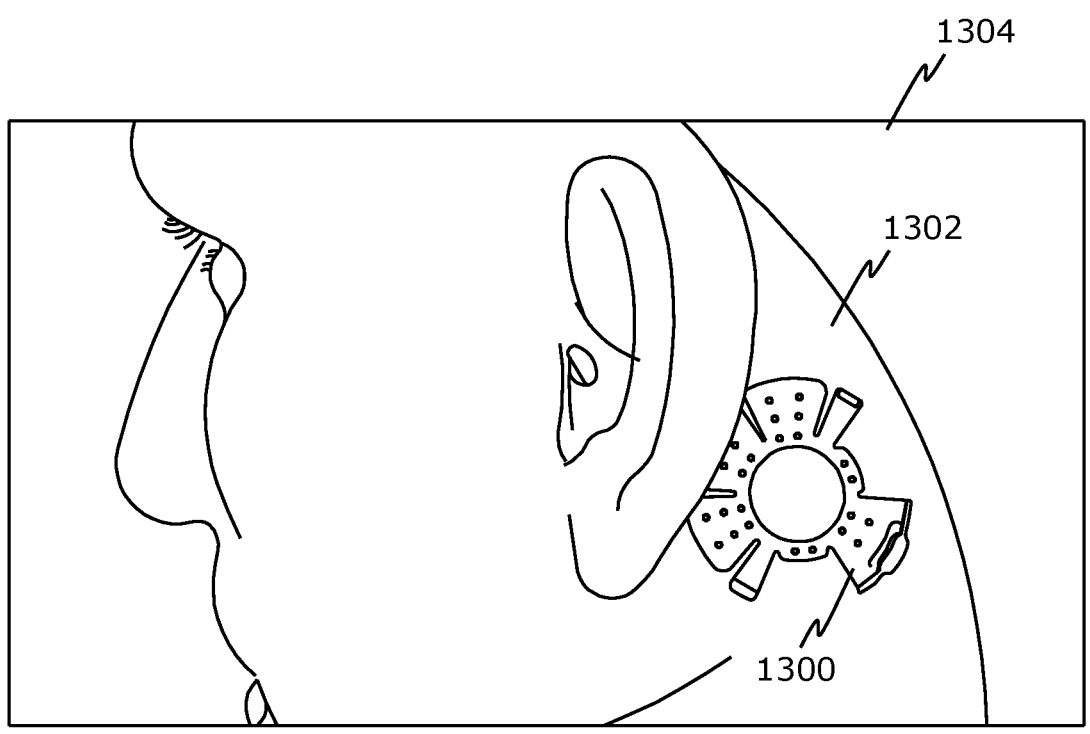
FIG. 13 is an arrangement of an adapter to a skin of a patient, in accordance with an embodiment of the present disclosure.

FIG. 13 is an arrangement of an adapter 1300 to a skin 1302 of a patient 1304, in accordance with an embodiment of the present disclosure. A first side (not shown) of the adapter 1300 is fastened to said skin 1302 using an adhesive material (not shown), and a second side of the adapter 1300 is in contact with a first unit (not shown) of an energy transmitting device (not shown) for securing said first unit.

Figure 14:
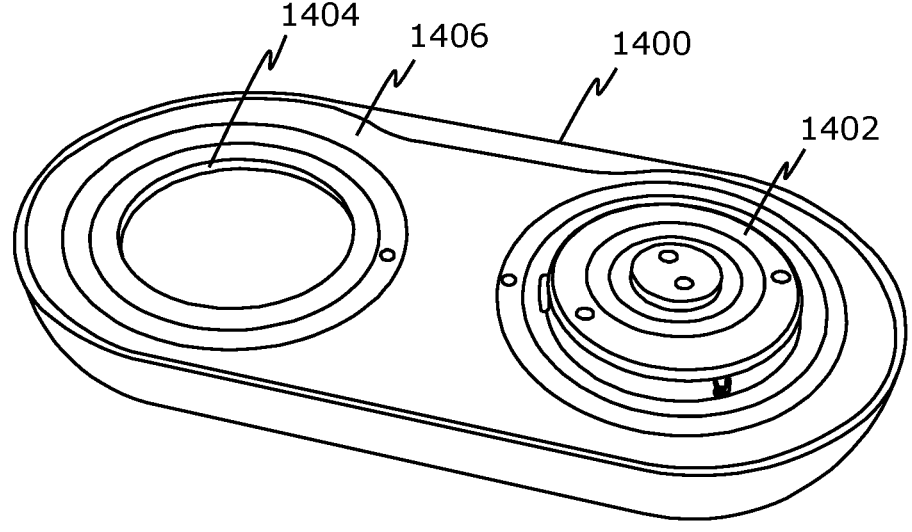
FIG. 14 is a charging device to charge a first unit, in accordance with an embodiment of the present disclosure.

FIG. 14 is a charging device 1400 to charge a first unit 1402, in accordance with an embodiment of the present disclosure. As shown, a first portion (not shown) of said first unit 1402 is accommodated in an indentation 1404 on a surface 1406 of said charging device 1400 for receiving an electric charge. Herein, said first portion is in direct contact with said surface 1406 for receiving said electric charge.

Figure 15:
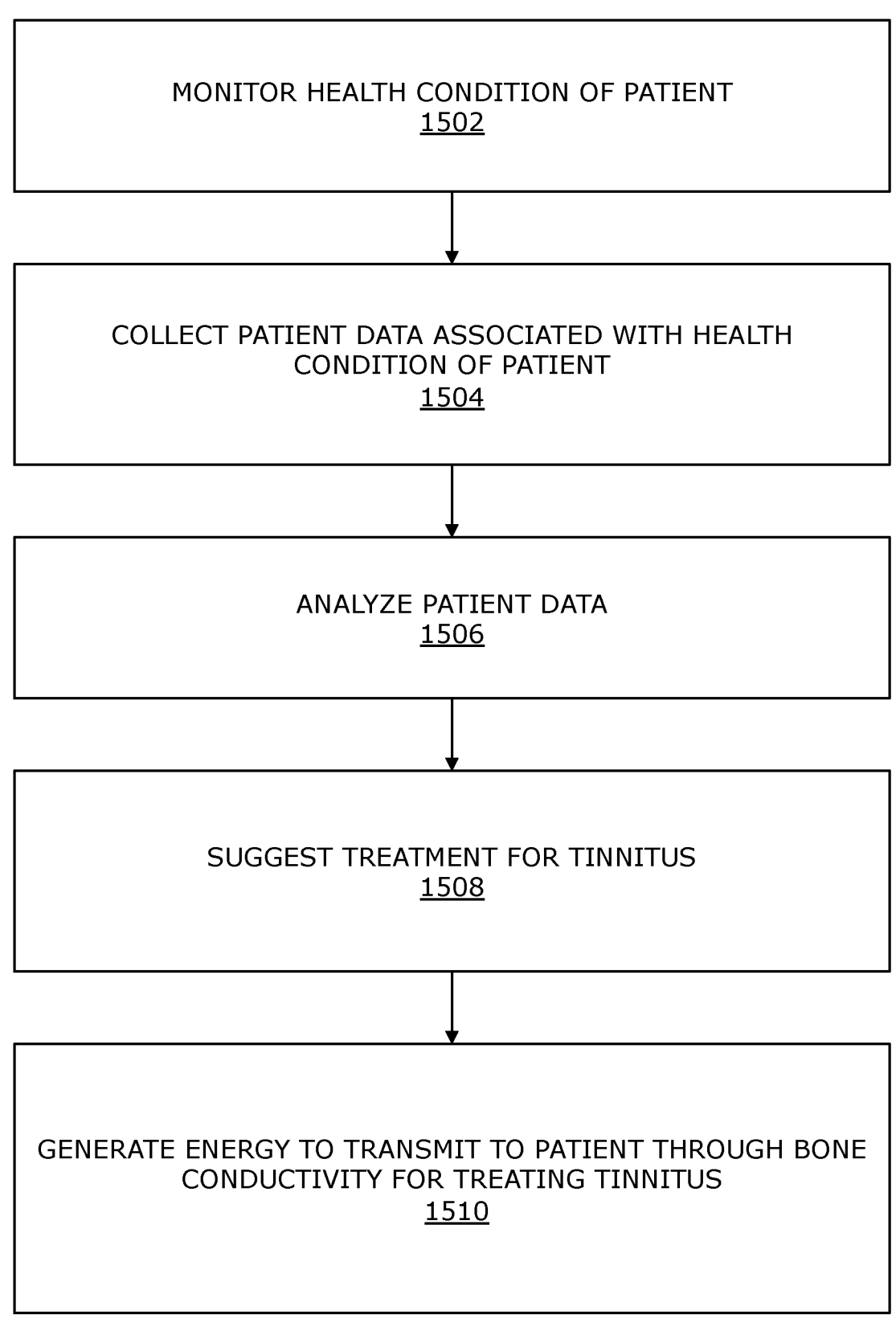
FIG. 15 is a flow diagram illustrating steps of a method for (of) monitoring and treating tinnitus, in accordance with an embodiment of the present disclosure.

FIG. 15 is a flow diagram illustrating steps of a method for (of) monitoring and treating tinnitus, in accordance with an embodiment of the present disclosure. At step 1502, an health condition of a patient is monitored using at least one sensor. At step 1504, the patient data associated with the health condition of the patient is collected. At step 1506, the patient data associated with the health condition of the patient is analysed. At step 1508, the treatment for tinnitus is suggested to the patient based on the patient data. At step 1510, the energy is generated based on the suggested treatment to transmit the energy to the patient through bone conductivity for treating the tinnitus.

The steps 1502, 1504, 1506, 1508, and 1510 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. An energy transmitting device for use in a system to monitor and treat tinnitus, comprising:
   a first unit having a first portion and a second portion that is attached to the first portion to form a cavity; and
   a second unit including an adapter having a first side and a second side;
   wherein the first unit includes a vibrating means accommodated in the cavity and connected to a peripheral region of the second portion, via a flexible ring, for enabling vibration of the vibrating means, and wherein the vibrating means is arranged in a central region of the second portion;
   wherein the second unit includes an adhesive material arranged to attach the first side of the adapter to the skin of the patient and thereby permitting the first unit to be attached to the skin of the patient by being arranged within the adapter;

wherein, when in use, the vibrating means of the first unit is arranged to be in direct contact, or indirect contact via the adhesive or adapter, with the skin of the patient; and wherein, when in operation, the first unit produces energy based on a suggested treatment for transmission to the patient through bone conductivity for treating the tinnitus.

2. An energy transmitting device according claim 1, wherein the adapter is integrated into the adhesive material for securing the first unit with the adhesive material, and is a magnetic adapter that secures the first unit through magnetism.

3. An energy transmitting device according to claim 1, wherein the adapter comprises a snap lock that locks the first unit within the adapter and enables removal of the first unit from the adapter after use.

4. An energy transmitting device according to claim 3, wherein the second unit comprises:

an adhesive material that includes a first hole; and an adapter, which includes a second hole, and is integrated into the adhesive material, for securing the first unit with the adhesive material;

wherein the snap lock is configured to receive the first unit and lock the first unit within the adapter; and wherein the first and the second holes enable the first unit, in use, to be in contact with the skin of the patient.

5. An energy transmitting device according to claim 1, wherein the adapter is integrated into the adhesive material for securing the first unit with the adhesive material and includes a lock that receives the first unit and locks the first unit within the adapter;

wherein the adhesive material includes a first side that is arranged to be in contact with the skin of the patient, and a second side that is integrated with the adapter and is in contact with the first unit;

wherein, when in operation, when the adhesive material is arranged to be in contact with the skin of the patient, the first unit produces the energy based on the suggested treatment, and the adhesive material is configured to transmit the energy from the first unit to the patient through bone conductivity for treating the tinnitus.

6. An energy transmitting device according to claim 1, wherein the adapter is made of a flexible material for transmission of vibrations from the vibrating means to the skin of the patient.

7. An energy transmitting device according to claim 1, wherein the first unit further comprises a first conductive plate, a second conductive plate, a battery unit, a printed circuit board device, and an energy transmitting unit that are accommodated in the cavity;

wherein the battery unit is accommodated between the first conductive plate and the second conductive plate, the printed circuit board device is coupled to the battery unit, and the energy transmitting unit is fastened to the vibrating means; and wherein the printed circuit board device and the second conductive plate are adapted to form a ring shape for accommodating the energy transmitting unit therein.

8. An energy transmitting device according to claim 1, wherein a locking ring is interposed between the first portion and the second portion.

9. An energy transmitting device according to claim 1, further comprising a charging device that, in operation, charges the energy transmitting device;

wherein the first portion of the energy transmitting device is to be at least partially accommodated in an indentation on a surface of the charging device for receiving an electric charge.

10. An energy transmitting device according to claim 1, wherein the first unit includes at least one of a first magnet or a first magnetic plate; and wherein the second unit includes a magnetic adapter that is integrated into the adhesive material for securing the first unit with the adhesive material;

wherein the magnetic adapter includes at least one of a second magnet or a second magnetic plate that enables magnetic attachment between the magnetic adapter and the first magnet or the first magnetic plate of the first unit;

wherein the adhesive material includes a first side that is arranged to be in contact with the skin of the patient, and a second side that is integrated with the magnetic adapter and is in contact with the first unit; and wherein the magnetic adapter is arranged to transmit the energy based on the suggested treatment to the patient through bone conductivity for treating the tinnitus.

11. An energy transmitting device according to claim 1, wherein the first unit produces the energy that is selected from at least one of white noise, electrical energy, electromagnetic energy, or light energy.

12. An energy transmitting device according to claim 11, wherein the first unit comprises a white noise generator that produces the white noise; and wherein the white noise ranges from 20 hertz (Hz) to 20,000 Hz.

13. An energy transmitting device according to claim 11, wherein the first unit comprises an electrostimulator that produces the electrical energy; and wherein the electrical energy ranges from 45 microamperes ($\mu$A) to 100 $\mu$A.

14. An energy transmitting device according to claim 11, wherein the first unit comprises a neurostimulator that produces the electrical energy, or the electromagnetic energy; and wherein the electrical energy ranges from 45 microamperes ($\mu$A) to 100 $\mu$A, or the electromagnetic energy ranges from 10 hertz (Hz) to 90 Hz.

15. An energy transmitting device according to claim 11, wherein the first unit comprises a laser emitting device that produces the light energy; and wherein the light energy has a wavelength range from 600 nanometres (nm) to 1000 nm.

16. An energy transmitting device according to claim 11, wherein said first unit comprises:

a plurality of buttons that is pre-programmed with a plurality of suggested treatment operations to treat the tinnitus; and a second processor that is configured to execute at least one of the suggested treatment operations when at least one button is actuated by the patient.

17. A system to monitor and treat tinnitus, the system comprising:

a sensor unit that includes at least one sensor to monitor a health condition associated with an auditory dysfunction of a patient;

a first processor and a database to collect patient data associated with the health condition associated with the auditory dysfunction of the patient and to suggest the suggested treatment for the tinnitus to the patient based on the collected patient data; and an energy transmitting device according to claim 1.

18. A system according to claim 17, further comprising an interface configured for the patient to provide, to the system, subjective information pertaining to a health condition of the patient;

wherein the first processor suggests the suggested treatment for the tinnitus to the patient based on the subjective information.

19. A system according to claim 17, wherein the first processor predicts a change in the tinnitus that is about to happen in future based on the patient data, indicates to the patient about the change in the tinnitus that is about to happen and to the patient to handle the tinnitus in the future.

20. A system according to claim 19, wherein the system further comprises an interface that enables the patient to provide information about when the changes in the tinnitus occur and transmits the information to a cloud server for analyzing the information to suggest the treatment for the tinnitus.

21. A system according to claim 17, wherein the at least one sensor comprises at least one of: an accelerometer, a temperature sensor, a pulse sensor, a blood pressure sensor, and an oxygenation sensor.

\* \* \* \* \*